United States Patent [19]
Lee et al.

[11] Patent Number: 5,908,769
[45] Date of Patent: Jun. 1, 1999

[54] SOLVENT-FREE METHOD FOR REACTING SHORT-CHAIN ALCOHOLS AND ACIDS USING *C. ANTARCTICA* LIPASE IMMOBILIZED TO ACRYLIC RESIN

[75] Inventors: Byung Hyung Lee, Taejon; Soon Ook Hwang; Nam Ryun Cho, both of Seoul, all of Rep. of Korea

[73] Assignee: Yukong Limited, Seoul, Rep. of Korea

[21] Appl. No.: 08/829,591

[22] Filed: Mar. 31, 1997

[30] Foreign Application Priority Data

Mar. 29, 1996 [KR] Rep. of Korea .......................... 96-9260

[51] Int. Cl.$^6$ ................................... C12P 7/62; C12P 7/64
[52] U.S. Cl. ........................... 435/135; 435/134; 435/921
[58] Field of Search ..................................... 435/134, 135, 435/280, 921

[56] References Cited

PUBLICATIONS

Paiva et al., "Process integration involving lipase–catalyzed ester synthesis reactions", Biotechnology Techniques 8 (9) : 629–634 (1994).

Gatfield, "The enzymatic syntheisi of esters in non–aquous systems", 1wt 19 (1) : 87–88 (1986).

Oguntimein et al., "Synthesis of geraniol esters in a solvent–free system catalyzed by *Candida antarctica* lipase", Biotechnology Lett. 17 (1) : 77–82 (1995).

*Primary Examiner*—Sandra E. Saucier
*Attorney, Agent, or Firm*—Abelman, Frayne & Schwab

[57] ABSTRACT

An ester compound is prepared with a greatly improved efficiency by reacting a liquid alcohol with a liquid organic acid at a temperature of about 30 to 70° C. in the presence of a lipase without adding any solvent. In particular, short chain acids and alcohols are reacted with lipase from candida antarctica immobilized on an acrylic resin.

4 Claims, No Drawings

SOLVENT-FREE METHOD FOR REACTING SHORT-CHAIN ALCOHOLS AND ACIDS USING C. ANTARCTICA LIPASE IMMOBILIZED TO ACRYLIC RESIN

BACKGROUND OF THE INVENTION

1. Field of the Invention

The present invention relates, in general, to a method for preparing an ester compound and, more specifically, to a method for preparing an ester compound by reacting a liquid alcohol with a liquid organic acid in the presence of lipase without adding any solvent.

Here, "ester compound" refers, for example, to ethyl, n-propyl, isopropyl, n-butyl,, iso-butyrated acetic acid, propionic acid, n-butyric acid, isobutyric acid, n-valeric acid, iso-valeric acid or the like, all of which are used as natural flavors.

2. Description of the Prior Art

Usually, an ester compound is synthesized by chemical or biological methods. In the latter method, for example, lipase an esterase is used for reaction of an alcohol with a carboxylic acid to produce an ester compound and water.

In Biotech. Lett., 12, 581 (1990), Langrand et al., discloses the synthesis of an ester compound, wherein ethanol is reacted with n-butyric acid to produce ethyl butyrate and water as shown in the following formula:

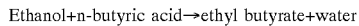

Ethanol+n-butyric acid→ethyl butyrate+water

This formula can be generally represented as follows:

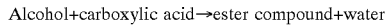

Alcohol+carboxylic acid→ester compound+water

The ester compound can also be prepared chemically. However, the preference to natural compounds induces researchers to biologically synthesize ester compounds using fermented materials of microorganisms or enzymes. For example, it is reported in a great number of literatures that ester compounds are prepared in an aqueous state (Armstrong et al., Biotechnol. Bioeng. 26, 1038 (1984); Williams et al., Ann. New York Acad. Sci., 542, 406 (1988); Murray and Duff, Appl. Microbiol. Biotechnol. 33. 202 (1990); Fukuda et al., Curr, Genet. 20, 49 (1991); Fukuda et al., J. Ferm. Bioeng. 75, 288 (1993)). These active researches demonstrated the production of ester but have a disadvantage in that the ester compounds produced are extremely low in solubility in water.

Other reaction systems than water include solvent phase (Carta et al., Biotechnol. Bioeng. 37, 1004 (1991); Langrand et al., Biotech. Lett. 12, 581 (1990); Carta et al., Enzyme Microb. Technol., 14, 904 (1992)), supercritical fluid phase (Marty et al., Biotechnol. Bioeng., 39, 273 (1992); Marty et al., Biotechnol. Bioeng., 43, 497 (1994)) and gas phase (Hwang and Park, Biotech. Lett., 16, 379, (1994)). However, the solvent phase reaction is disadvantageous in that a large amount of cost is required to separate and collect the product from the reaction system (solution). The application of the supercritical fluid phase reaction or the gas phase reaction for an industrial process scale is still in a beginning stage. Accordingly, using only liquid phase substrates in the absence of solvent can bring about the advantages of reducing production cost, being safe and facilitating separation and collection. Thus, the natural flavors can be produced on a large scale in this manner (see: Carta et al., Enzyme Microb. Technol., 14, 904 (1992); Oguntimein et al., Biotech. Lett., 17, 77 (1995)).

SUMMARY OF THE INVENTION

The intensive and thorough research of the present inventors for solving the above probtlems encountered in prior arts results in the development of a non-solvent system in which an ester compound can be produced from a liquid alcohol and an organic acid using lipase in the absence of solvent.

Therefore, it is an objective to provide a method for preparing an ester compound by reaction of a liquid alcohol with an organic acid in the presence of lipase without a solvent.

In accordance with an aspect of the present invention, the above objective can be accomplished by a provision of a method for preparing an ester compound in a non-solvent phase, comprising reacting a liquid alcohol selected from the group consisting of ethanol, propanol, iso-propanol, butanol and iso-butanol with a liquid organic acid selected from the group consisting of acetic acid, propionic acid, iso-butyric acid, and iso-valeric acid at a temperature of about 30 to 70° C. in the presence of lipase without adding any solvent.

In accordance with another aspect of the present invention, there is provided a method for preparing an ester compound in a non-solvent phase, comprising reacting a liquid alcohol selected from the group consisting of ethanol, iso-propanol, and iso-butanol with a liquid organic acid selected from the group consisting of n-butyric acid and n-valeric acid at a temperature of about 30 to 70° C. in the presence of lipase without adding any solvent.

DETAILED DESCRIPTION OF THE INVENTION

According to the present invention, there is provided a non-solvent system in which a liquid alcohol and a liquid organic acid are reacted at a temperature of about 30 to 70° C. in the presence of lipase without any solvent.

The lipases useful for the present invention include those that are extracted from pig pancreas or from microorganisms and the biological cells that contain lipases. They may be provided as a form of powder or liquid or as an immobilized one. Particularly, in this regard, lipase is preferably immobilized to a carrier especially, an acrylic resin.

For the lipase, commercially available ones and, if necessary, home-made ones can be used. Non-limiting examples of the commercially available lipases include those manufactured by Amano Company, such as Lipase AY, Lipase CES and Lipae PS, Lipase and Novozym 435 from Novo Company, Jozo from Toyo Company, and Lipase PPL from Sigma Company with preference to Novozym 435, which is immobilized to an acrylic resin as a carrier.

As one substrate component of the present invention, alcohols include ethanol, propanol, isopropanol, butanol and iso-butanol and preferably ethanol, isopropanol and iso-butanol. Of the alcohols, propanol and butanol are reported to react with particular organic acids, for example, butyric acid and valeric acid, in non-solvent systems, to produce ester compounds (Gatfield, in "Bioformation of Flavors", p175 (1992), Royal Society of Chemistry) but nowhere is mentioned a detail of production method and yield. It has not been reported that ethanol, isopropanol or iso-butanol is used for the production of an ester in a non-solvent phase using enzyme because even a low concentration of such alcohol can inactivate the enzyme.

Duarte disclosed in "Perspectives in Biotechnology" (vol. 128 Plenum Press p 23 (1987)) that water-miscible organic solvents, such as ethanol, break down the hydrophilic interaction between protein molecules (enzyme) and their hydration layer and penetrate into the hydration layer, resulting in destructurizing the protein molecules. Carta et al., described in Enzyme Microb. Technol. 14 904 (1992) that ethanol inactivates enzymes even at a low concentration because it deleteriously affects immobilized enzymes.

In an esterreaction, water plays a dual function of reversely acting in the thermodynamic equilibrium and aiding the catalytic action of enzyme. For organic phase reaction, a very little amount of water is known to be necessary (Abramowicz and Keese, Biotechnol. Bioeng. 33, 149 (1989)). It is also known that organic solvents make mobile a certain amount of the water bound to enzyme and, in this case, polar solvents separate more water from enzyme than nonpolar solvents (Gorman and Dordick, Biotechnol. Bioeng. 39, 392 (1992)). Consequently, the catalytic action of the enzyme in polar organic phase is dependent upon the relative significance between the mobile bound water and the structural bound water (Carta et al., Enzyme Microb. Technol. 14, 904 (1992)).

For these reasons, most of the reaction using polar solvents, especially, ethanol, are reported to be virtually impossible to achieve (Gatfield, in "Bioformation of Flavors" Royal Society of Chemistry, p 175 (1992)).

Although slightly low in production yield, ester compounds can be obtained by reaction of alcohols with organic acids in the presence of lipase under non-solvent systems, according to the present invention. Particularly, when lipase is immobilized to a hydrophobic carrier, ester compounds can be produced at very high yields. Use of the lipase immobilized to a hydrophobic carrier, such as acrylic resin, allows the mobile fraction rather than the structural fraction of the bound water to be released into the organic solvent phase, the reactant, so that the water-miscible reactant such as ethanol is prevented from attacking the enzyme. In the case of using a hydrophilic carrier, the water which is produced during the reaction exists around the enzyme, showing production inhibition and induces the organic solvent to penetrate into the hydration layer so that the enzyme becomes inactivated. On the other hand, when the enzyme is immobilized to a hydrophobic carrier the reaction can continuously proceed because the water produced is separated from the enzyme by virtue of the hydrophobicity of the immobilized enzyme. After the reaction completely proceeds, it can be observed that the water produced is separated from the ester compound and the reactants and gathered, as the reactants are reduced. Thus, since the water produced has less influence upon the enzyme, immobilization of enzyme to hydrophobic carrier is preferred to the reaction.

Examples of the organic acids useful in the present invention include acetic acid, propionic acid, n-butyric acid, iso-butyric acid, n-valeric acid and iso-valeric acid. As to the amount of the alcohol and the organic acid, it is preferred to add alcohol at 1 to 15-fold, preferably 2 to 5-fold excess moles when reaction rate and efficiency are taken into account.

In an embodiment of the present invention, a liquid alcohol and a liquid organic acid are reacted at room temperature or higher in a 15 ml vial which is sealed with a silicon/teflon rubber stopper to prevent air flow and contains a lipase therein. The reaction temperature is preferably maintained at a temperature of 30 to 70° C. 24 hours is enough to complete the reaction. The ester compound produced may be readily separated from unreacted substrates by distillation.

The ester compounds thus prepared include ethyl acetate, n-propyl acetate, iso-propyl acetate, n-butyl acetate, iso-butyl acetate, ethyl propionate, n-propyl propionate, iso-propyl propionate, n-butyl propionate, iso-butyl propionate, ethyl n-butyrate, iso-propyl n-butyrate, iso-butyl n-butyrate, ethyl iso-butyrate, n-propyl iso-butyrate, iso-propyl iso-butyrate, n-butyl iso-butyrate, iso-butyl iso-butyrate, ethyl n-valerate, iso-propyl n-valerate, iso-butyl n-valerate, ethyl iso-valerate, n-propyl iso-valerate, iso-propyl iso-valerate, n-butyl iso-valerate, and iso-butyl iso-valerate.

A gas chromatography analysis is available to quantify the ester compounds prepared according to the present invention. A capillary column filled with carbowax-coated silica is heated from 40° C. up to 160° C. in an elevation rate of 10° C. per min. and then, the temperature is maintained for 2 min. Helium gas is used as a carrier with a flow rate of 1 ml/min. Detection is made by using a flame ionization detector (FID) at 200° C. Ethanol, n-butyric acid and ethyl n-butyrate are detected at 4.7 min., 13.3 min. and 5.5 min. after injection, respectively.

A better understanding of the present invention may be obtained through the following examples which are set forth to illustrate, but are not to be construed as the limit of the present invention.

EXAMPLE I 20 mg of Novozym 435, commercially available from Novo Company, was placed in a 15 ml vial which was sealed with a silicon/teflon rubber stopper to prevent air flow. 4.5 ml of ethanol, sold by Fluka Company, and 0.5 ml of n-butyric acid, sold by Junsei Company, Japan, were added in the vial and reacted with each other at 30° C. with stirring. A predetermined amount of the contents of the vial was taken at a predetermined time, chilled on ice to stop reaction process, and centrifuged to separate enzyme and the product. The supernatant was quantitated using a gas chromatograph sold by Hewlett-Packard, identified as Model 5890. The amounts of the product, ethyl butyrate produced according to reaction time were measured and the results are given as shown in Table I below.

For the gas chromatography analysis, a capillary column (Nukol, inner diameter 0.53 mm, film thickness 0.5 mm, length 30 m, sold by Supelco) filled with carbowax-coated silica was heated from 40° C. up to 160° C. at an elevation rate of 10° C. per min. and then, the temperature was maintained for 2 min. As a carrier, helium gas was used with a flow rate of 1 ml/min.

TABLE 1

Amounts of the Product varying with Reaction Time

| Reaction Time (hrs) | Ethyl butyrate (M) |
| --- | --- |
| 3 | 0.1865 |
| 6 | 0.2520 |
| 9 | 0.4229 |
| 24 | 0.8897 |

EXAMPLES II THROUGH IX

The procedure of Example I was repeated except that the enzyme was used at amounts indicated in Table 2 below and the contents in the vial were taken 9 hours after reaction and chilled on ice to stop the reaction. The results are given as shown in Table 2 below.

TABLE 2

Amounts of the Product varying with Amounts of Enzyme

| Example No. | Amount of Enzyme (mg) | Ethyl butyrate (M) |
|---|---|---|
| II | 1 | 0.0203 |
| III | 2 | 0.0711 |
| IV | 5 | 0.1208 |
| V | 10 | 0.1741 |
| VI | 20 | 0.4299 |
| VII | 50 | 0.9761 |
| VIII | 100 | 1.4519 |
| IX | 200 | 2.2483 |

EXAMPLE X

The procedure of Example I was repeated except that n-valeric acid was used instead of butyric acid. Ethyl valerate was detected 6.8 min. after injection

EXAMPLES XI THROUGH XV 3 ml of ethanol and 2 ml of n-valeric acid were used as reactants and the reaction was carried out at temperatures ranging from 30 to 70° C. 9 hours after reaction, the product (ethyl n-valerate) was measured and analyzed according to the manner of Example I. The results are given as shown in Table 3 below.

TABLE 3

Amounts of the Product varying with Reaction Temperature

| Example No. | Reaction Temperature (° C.) | Ethyl n-valerate (M) |
|---|---|---|
| XI | 30 | 2.46 |
| XII | 40 | 2.61 |
| XIII | 50 | 2.79 |
| XIV | 60 | 2.81 |
| XV | 70 | 2.92 |

EXAMPLE XVI THROUGH XXI

The procedure of Example I was repeated except that the mole ratio of ethanol to n-butyric acid was controlled to range from 1.1 to 14.2. 9 hours after reaction, gas chromatography analysis was carried out in the same manner as that of Example I. The results are given as shown in Table 4 below.

TABLE 4

Amounts of the Product varying with Mole Ratio of Reactants

| Example No. | Mole Ratio of EtOH:n-BuCOOH | Ethyl butyrate (M) |
|---|---|---|
| XVI | 1.1 | 0.0641 |
| XVII | 1.6 | 0.5243 |
| XVIII | 2.4 | 1.1860 |
| XIX | 3.7 | 1.2357 |
| XX | 6.3 | 0.9419 |
| XXI | 14.2 | 0.4299 |

EXAMPLE XXII THROUGH XXVI

The procedure of Example I was repeated except that lipase was used as indicated in Table 5 below. 9 hours after reactions gas chromatography analysis was carried out. The results are given as shown in Table 5 below.

TABLE 5

Amounts of the Product according to Lipases

| Example No. | Lipase | Ethyl butyrate (mM) |
|---|---|---|
| XXII | Lipase PPL (Sigma) | 4.2881 |
| XXIII | Lipase MY (Meito) | 7.8160 |
| XXIV | Lipase AY (Amano) | 3.1432 |
| XXV | Lipase (Novo) | 7.0656 |
| XXVI | no lipase | 1.2443 |

EXAMPLE XXVII

The procedure of Example I was repeated except using acetic acid instead of n-butyric acid. The ethyl acetate was detected at 3.2 min. after injection.

EXAMPLE XXVIII

The procedure of Example I was repeated except using n-propanol and acetic acid instead of ethanol and n-butyric acid, respectively. The n-propyl acetate was detected at 4.2 min. after injection.

EXAMPLE XXIX

The procedure of Example I was repeated except using iso-propanol and acetic acid instead of ethanol and n-butyric acid, respectively. The iso-propyl acetate was detected at 3.3 min. after injection.

EXAMPLE XXX

The procedure of Example I was repeated except using n-butanol and acetic acid instead of ethanol and n-butyric acid, respectively. The butyl acetate was detected at 5.4 min. after injection.

EXAMPLE XXXI

The procedure of Example I was repeated except using iso-butanol and acetic acid instead of ethanol and n-butyric acid, respectively. The iso-butyl acetate was detected at 4.7 min. after injection.

EXAMPLE XXXII

The procedure of Example I was repeated except using propionic acid instead of n-butyric acid. The ethyl propionate was detected at 4.0 min. after injection.

EXAMPLE XXXIII

The procedure of Example I was repeated except using n-propanol and propionic acid instead of ethanol and n-butyric acid, respectively. The propyl propionate was detected at 5.0 min. after injection.

EXAMPLE XXXIV

The procedure of Example I was repeated except using iso-propanol and propionic acid instead of ethanol and n-butyric acid, respectively. The iso-propyl propionate was detected at 4.0 min after injection.

EXAMPLE XXXV

The procedure of Example I was repeated except using n-butanol and propionic acid instead of ethanol and n-butyric acid, respectively. The butyl propionate was detected at 6.5 min. after injection.

EXAMPLE XXXVI

The procedure of Example I was repeated except using iso-butanol and propionic acid instead of ethanol and n-butyric acid, respectively. The iso-butyl propionate was detected at 5.9 min after injection.

EXAMPLE XXXVII

The procedure of Example I was repeated except using iso-propanol instead of ethanol. The iso-propyl butyrate was detected at 5.2 min. after injection.

EXAMPLE XXXVIII

The procedure of Example I was repeated except using iso-butanol instead of ethanol. The isobutyl butyrate was detected at 7.1 min. after injection.

EXAMPLE XXXIX

The procedure of Example I was repeated except using iso-butyric acid instead of n-butyric acid. The ethyl iso-butyrate was detected at 4.3 min. after injection.

EXAMPLE XXXX

The procedure of Example I was repeated except using n-propanol and iso-butyric acid instead of ethanol and n-butyric acid, respectively. The propyl iso-butyrate was detected at 5.1 min. after injection.

EXAMPLE XXXXI

The procedure of Example I was repeated except using iso-propanol and iso-butyric acid instead of ethanol and n-butyric acid, respectively. The iso-propyl iso-butyrate was detected at 4.0 min. after injection.

EXAMPLE XXXXII

The procedure of Example I was repeated except using n-butanol and isobutyric acid instead of ethanol and n-butyric acid, respectively The butyl iso-butyrate was detected at 6.8 min. after injection.

EXAMPLE XXXXIII

The procedure of Example I was repeated except using iso-butanol and iso-butyric acid instead of ethanol and n-butyric acid, respectively. The iso-butyl iso-butyrate was detected at 6.0 min. after injection.

EXAMPLE XXXXIV

The procedure of Example I was repeated except using iso-propanol and n-valeric acid instead of ethanol and n-butyric acid, respectively. The iso-propyl n-valerate was detected at 6.7 min. after injection.

EXAMPLE XXXXV

The procedure of Example I was repeated except using iso-butanol and n-valeric acid instead of ethanol and n-butyric acid, respectively. The iso-butyl n-valerate was detected at 8.7 min. after injection.

EXAMPLE XXXXVI

The procedure of Example I was repeated except using iso-valeric acid instead of n-butyric acid. The ethyl iso-valerate was detected at 5.5 min. after injection.

EXAMPLE XXXXVII

The procedure of Example I was repeated except using n-propanol and iso-valeric acid instead of ethanol and n-butyric acid, respectively. The propyl iso-valerate was detected at 7.1 min. after injection.

EXAMPLE XXXXVIII

The procedure of Example I was repeated except using iso-propanol and iso-valeric acid instead of ethanol and n-butyric acid, respectively. The iso-propyl iso-valerate was detected at 5.5 min. after injection.

EXAMPLE XXXXIX

The procedure of Example I was repeated except using n-butanol and iso-valeric acid instead of ethanol and n-butyric acid, respectively. The butyl iso-valerate was detected at 8.7 min. after injection.

EXAMPLE XXXXX

The procedure of Example I was repeated except using iso-butanol and iso-valeric acid instead of ethanol and n-butyric acid, respectively. The iso-butyl iso-valerate was detected at 7.8 min. after injection.

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A method for preparing an ester compound in a solvent-free system, comprising directly reacting a liquid alcohol with a liquid organic acid as media at a temperature of about 30 to 70° C. in the presence of a lipase derived from *Candida antarctica* immobilized to an acrylic resin, said liquid alcohol being selected from the group consisting of ethanol, propanol, iso-propanol, butanol and iso-butanol and said liquid organic acid being selected from the group consisting of acetic acid, propionic acid, iso-butyric acid, and iso-valeric acid.

2. The method in accordance with claim 1, wherein said alcohol is used at 1 to 15-fold excess moles than said organic acid.

3. A method for preparing an ester compound in a solvent-free system, comprising directly reacting a liquid alcohol with a liquid organic acid as media at a temperature of about 30 to 70° C. in the presence of a lipase derived from *Candida antarctica* immobilized to an acrylic resin, said liquid alcohol being selected from the group consisting of ethanol, iso-propanol and iso-butanol and said liquid organic acid being selected from the group consisting of n-butyric acid and n-valeric acid.

4. The method in accordance with claim 3, wherein said alcohol is used at 1 to 15-fold excess moles than said organic acid.

* * * * *